(12) United States Patent
O'Dell et al.

(10) Patent No.: US 11,298,256 B1
(45) Date of Patent: Apr. 12, 2022

(54) SAFE MOBILITY TRANSPORT HARNESS

(71) Applicant: Safe Restraints, Inc., Walnut Creek, CA (US)

(72) Inventors: Ronald O'Dell, Danville, CA (US); Charles Hammond, Danville, CA (US)

(73) Assignee: Safe Restraints, Inc., Walnut Creek, CA (US)

(*) Notice: Subject to any disclaimer, the term of this patent is extended or adjusted under 35 U.S.C. 154(b) by 0 days.

(21) Appl. No.: 17/308,463

(22) Filed: May 5, 2021

(51) Int. Cl.
*A61F 5/37* (2006.01)
*E05B 75/00* (2006.01)

(52) U.S. Cl.
CPC .......... *A61F 5/3723* (2013.01); *E05B 75/00* (2013.01)

(58) Field of Classification Search
CPC .......... A61F 5/37; A61F 5/3723; A61F 5/373; A61F 5/05858; A61F 5/05866; A61F 5/3776; E05B 75/00; A47D 13/046; A47D 13/086; A47D 15/005; A61H 2201/1652; A61B 5/6831
USPC .................................................. 128/875, 876
See application file for complete search history.

(56) References Cited

U.S. PATENT DOCUMENTS

| | | | | |
|---|---|---|---|---|
| 5,031,639 A | * | 7/1991 | Wolfer | E05B 75/00 128/874 |
| 5,469,813 A | * | 11/1995 | Peden | E05B 75/00 119/770 |
| 5,829,443 A | * | 11/1998 | Cunningham | A61F 5/3715 128/869 |
| 6,368,262 B1 | * | 4/2002 | Willoughby | A01K 15/04 119/796 |
| 7,000,438 B1 | * | 2/2006 | Cooper | E05B 75/00 128/869 |
| 7,520,149 B1 | * | 4/2009 | Roemmele | B43K 7/005 401/195 |
| 7,581,416 B1 | * | 9/2009 | Lenertz | E05B 75/00 119/770 |
| 2006/0289017 A1 | * | 12/2006 | Schmeltz | A61F 5/3723 128/869 |
| 2010/0319412 A1 | * | 12/2010 | Espinosa | E05B 75/00 70/16 |
| 2019/0091058 A1 | * | 3/2019 | Figueroa | A61F 5/3723 |
| 2019/0388716 A1 | * | 12/2019 | Barrow | E06C 1/56 |
| 2021/0078163 A1 | * | 3/2021 | Ohtsubo | B25J 9/0006 |

OTHER PUBLICATIONS

U.S. Department of Justice, "Positional Asphyxia—Sudden Death," U.S. Department of Justice, Office of Justice Programs, National Institute of Justice, Jun. 1995, https://www.ojp.gov/pdffiles/posasph.pdf, accessed Oct. 12, 2021.

(Continued)

*Primary Examiner* — Alireza Nia
*Assistant Examiner* — Robin Han
(74) *Attorney, Agent, or Firm* — Gerald R. Prettyman

(57) ABSTRACT

A safe mobility transport harness allows for safely restraining persons and for safely restraining the person's arms and legs to prevent a person from escape or being combative by using his or her elbows, arms or legs to suddenly run or unexpected elbow or kick another person, and yet, when in need to transport, the restraints may be safely and easily adjusted to allow for authorized, safe and limited movement and walking of the restrained person.

7 Claims, 5 Drawing Sheets

(56) References Cited

OTHER PUBLICATIONS

Emily R. Siegel and Joseph Neff, NBC News, "'He died like an animal': Some police still 'hogtie' people despite risks." https://www.nbcnews.com/news/US-news/he-died-animal-somepolice-still-hogtie-people-despite-risks-n1268032, dated May 24, 2021, accessed Sep. 24, 2021.

Amnesty International, "Police Brutality and Excessive Force in the New York City Police Department." Jun. 1, 1996, Last Updated: Wednesday, Dec. 8, 2021, AMR/51/36/96, https://www.refworld.org/docid/3ae6a9e18.html, last accessed Dec. 9, 2021.

Matt Lait, "Controversial Police Restraint to Be Banned", Los Angles Times, Jul. 4, 1997, https://www.latimes.com/archives/la-xpm-1997-jul-04-me-9731-story.html, accessed Dec. 9, 2021.

"Hog-tying may be too dangerous a practice," The Bakersfield Californian, Jun. 8, 2013, https://www.bakersfield.com/archives/hog-tying-may-be-too-dangerous-a-practice/article_ec3b107f-ad31-5244-8921-76b64ada3ae5.html, last accessed Dec. 9, 2021.

Lawrence E. Heiskell, "How To Prevent Positional Asphyxia," POLICE Magazine, Sep. 9, 2019, https://www.policemag.com/524139/how-to-prevent-positional-asphyxia, last accessed Dec. 9, 2021.

"Davis Police Announce Change to Use of Force Policy—Ban Use of Carotid Control Hold," City of Davis Police Department, Jun. 6, 2020, https://www.davisenterprise.com/files/2020/06/Davis-Police-Ban-Carotid-Hold.pdf, last accessed Dec. 11, 2021.

"AB-490 Law enforcement agency policies: arrests: positional asphyxia," State of California, Oct. 1, 2021, https://leginfo.legislature.ca.gov/faces/billTextClient.xhtml?bill_id=202120220AB490, last accessed Dec. 11, 2021.

* cited by examiner

SAFE MOBILITY TRANSPORT HARNESS

CROSS-REFERENCE TO RELATED APPLICATION

Not Applicable

STATEMENT REGARDING FEDERALLY SPONSORED RESEARCH OR DEVELOPMENT

Not Applicable

BACKGROUND OF THE INVENTION

Field of Invention

The invention relates generally to the field of devices for safely restraining combative persons and more specifically to devices secured around a person's torso and for safely restraining the person's arms and legs.

Description of Related Art

Devices for restraining combative persons have for many decades (and centuries) attempted to prevent escape of a restrained person and injuries to other persons from a sudden or unexpected kick or elbowing by the restrained person. Most all devices (as well as the restrained person and the persons attempting to install the restraint) suffered multiple flaws. If the device was easily placed onto a conscious person, the device either injured the person (or worse—killed him), or failed to prevent sudden or unexpected kick or elbowing by the restrained person. Worse yet were the devices that were difficult to place onto a conscious person. The device often injured or ultimately killed the person, while the persons attempting to install the restraint often suffered from kick and elbowing by the restrained person. We've been sending people to space for 6 decades—it's time for a device that can safely restrain a combative person for everyone's safety.

SUMMARY OF THE INVENTION

Embodiments are directed to a safe mobility transport harness (100) for safely restraining persons around a person's torso and for safely restraining the person's arms and legs to prevent a person from unauthorized use of his or her elbows, arms or legs to run or be combative, or to suddenly or unexpected elbow or kick another person, and yet, when in need to transport, the restraints may be safely and easily adjusted to allow authorized, safe and limited movement of the restrained person.

A safe mobility transport harness (100) has a front connecting panel (105), a back lower connecting panel (175), a plurality of shoulder harness straps (110, 115, 155, 160) connecting the front connecting panel (105) to the back lower connecting panel (175) over the head of a restrained person, and a pair of adjustable side straps (125, 130), also for connecting the front connecting panel (105) to the back lower connecting panel (175) around the sides of the restrained person.

Affixed to a second adjustable side strap (125) is a second adjustable side strap tab (135) for affixing the second adjustable side strap (125) to a second restraint buckle (180) which is affixed to the back lower connecting panel (175). The second side adjustable strap (125) is slideably adjustable to allow for adjustable and safe restraint with limited movement of the restrained person. Affixed to a first adjustable side strap (130) is a first adjustable side strap tab (140) for affixing the first adjustable side strap (130) to a first restraint buckle (185) which is affixed to the back lower connecting panel (175). The first side adjustable strap (130) is slideably adjustable to allow for adjustable and safe restraint with limited movement of the restrained person. Each of the second restraint buckle (180) and the first restraint buckle (185) also have a restraint buckle recessed release mechanism (280) to prevent accidental release or intentional release by an unauthorized person of the second restraint buckle (180) and the first restraint buckle (185).

A third adjustable strap, a middle adjustable strap (145) and having a middle adjustable strap tab (150) for affixing to a middle restraint buckle (190) on the back lower connecting panel (175), is affixed to midpoint of the front connecting panel (105), for use with an ankle restraint cuff (210) having an ankle restraint cuff loop (215) to restrain leg mobility of the restrained person to prevent running, attempted escape and injurious and damaging activity such as kicking by a restrained person. The middle adjustable strap (145) is slideably adjustable to allow for authorized and safe restraint with limited leg movement of the restrained person, such as walking. The ankle restraint cuff (210) also has an ankle restraint cuff distinguishable lift tab (275) to readily distinguish a proximal end of the ankle restraint cuff (210) from an inner portion of the ankle restraint cuff (210).

Also affixed to the front connecting panel (105) and the back lower connecting panel (175) are a first hand-restraint retaining ring (120) and a second hand-restraint retaining ring (270), either or both of which may be used with either of a first accessory hand restraint (220) or a second accessory hand restraint (295) to prevent or permit as desired the restrained person from using either or both hands, while allowing placement of a restrained hand in front of, or behind the restrained person as indicated by the location or situation, such as transport, jail, or court, etc.

An arm accessory restraint (225) has a first arm adjustable length cuff (230), a second arm adjustable length cuff (235), and an adjustable length connecting strap (240) which may be used to secure one or both arms of a restrained person to prevent elbowing or limited use or one to both arms as indicated by the location or situation, such as transport, jail, or court, etc. The arm accessory restraint (225) may also be used with second hand-restraint retaining ring (270) to further limit arm movement.

DETAILED DESCRIPTION OF THE INVENTION

Figure 1:
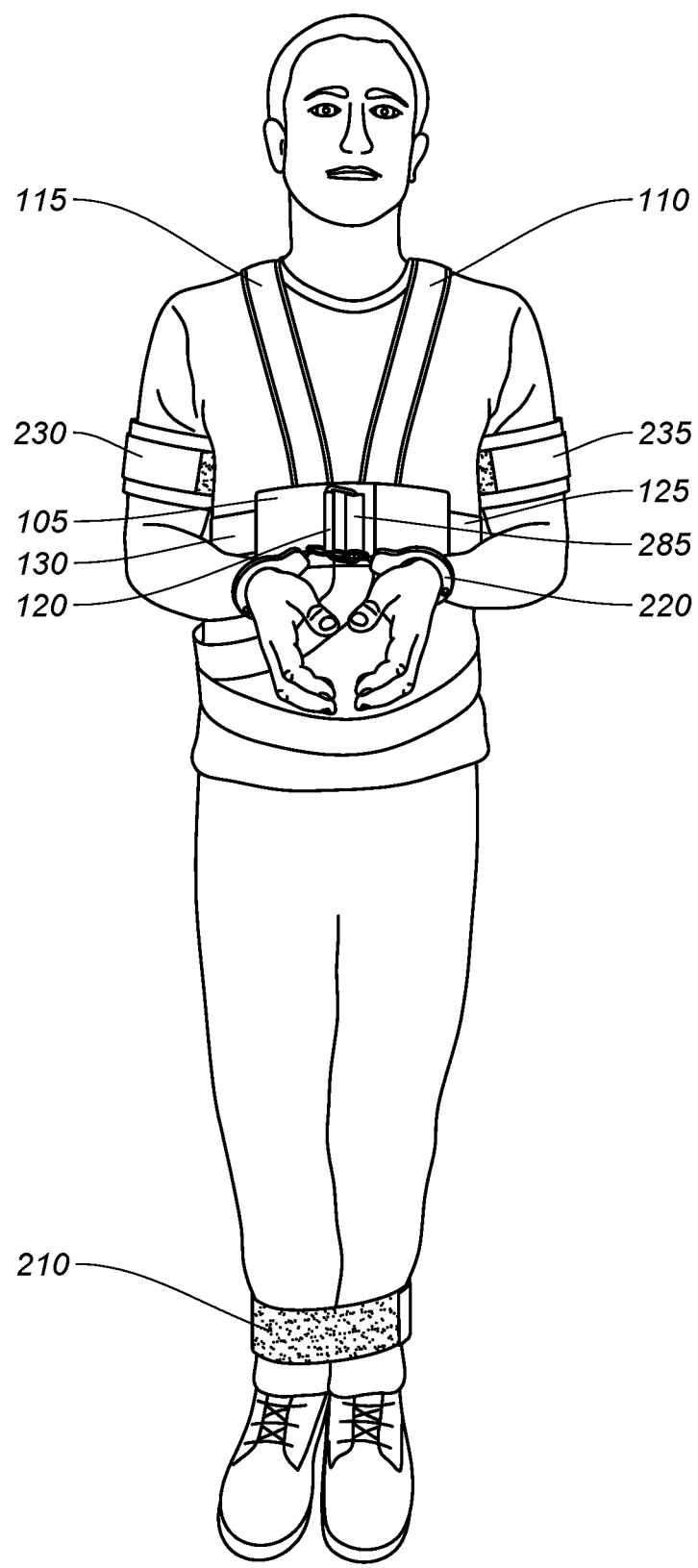
FIG. 1 shows a front view of a safe mobility transport harness secured around a person's torso with an ankle cuff around both legs of the person. An ankle restraint strap from the strap safe mobility transport harness may be secured to the ankle cuff behind the person.

FIG. 1 shows a front view of a safe mobility transport harness secured around a person's torso with an ankle cuff around both legs of the person. An ankle restraint strap may be secured to the ankle cuff behind the person.

Shown in FIG. 1 are the safe mobility transport harness (100), a front connecting panel (105), a front second side shoulder harness strap (110), a front first side shoulder harness strap (115), a first hand-restraint retaining ring (120), a second side adjustable strap (125), a first side adjustable strap (130), an ankle restraint cuff (210), first accessory hand restraint (220), and an arm accessory restraint (225) comprising a first arm adjustable length cuff (230) and a second arm adjustable length cuff (235).

Figure 2:
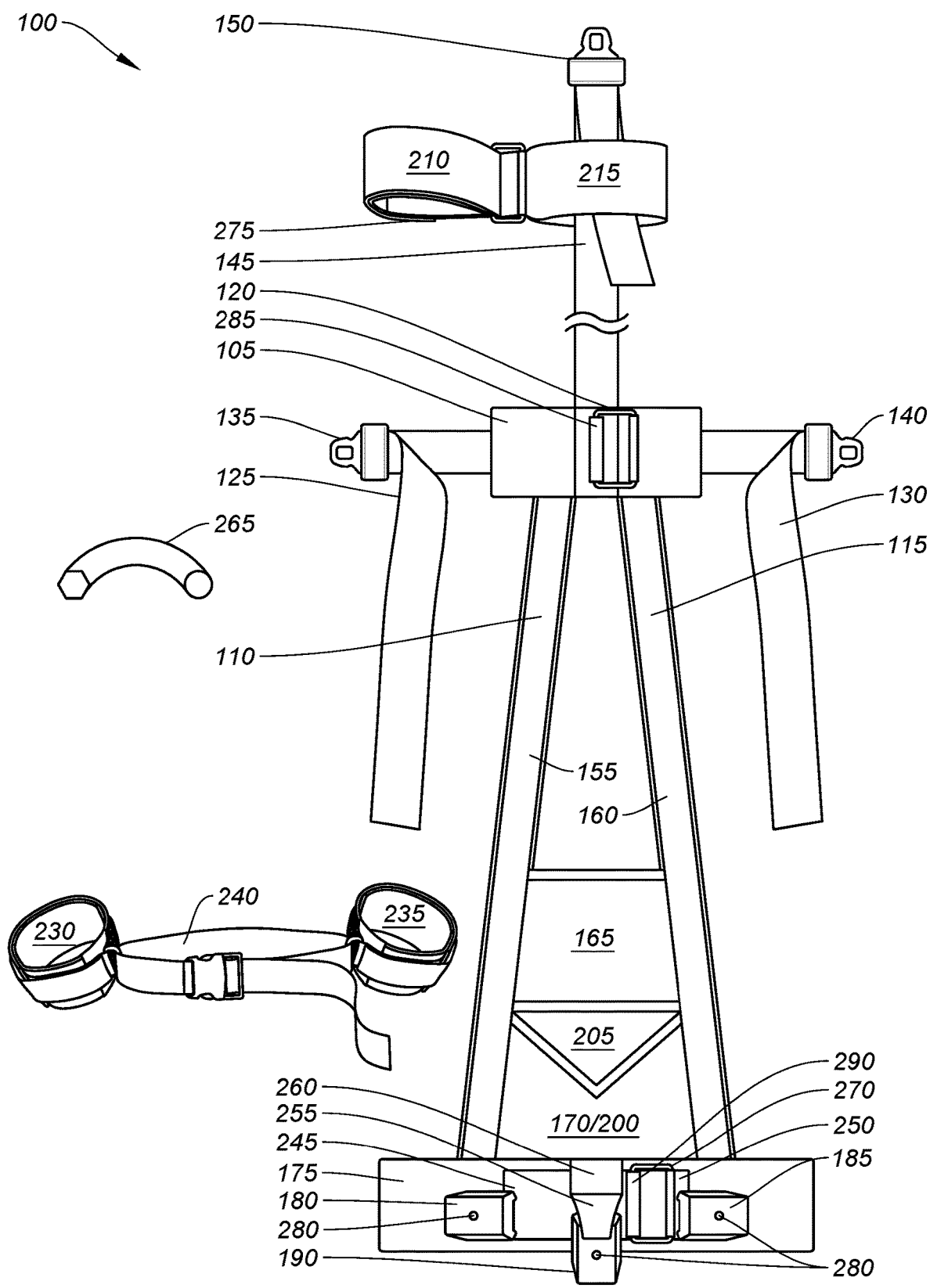
FIG. 2 shows a front view of a safe mobility transport harness as if laid flat for showing and identifying the components of the safe mobility transport harness.

FIG. 2 shows a front view of a safe mobility transport harness as if laid flat for showing and identifying the components of the safe mobility transport harness.

Shown in FIG. 2 are the safe mobility transport harness (100), the front connecting panel (105), the front second side shoulder harness strap (110), the front first side shoulder harness strap (115), the first hand-restraint retaining ring (120), second side adjustable strap (125), a first side adjustable strap (130), a second side adjustable strap tab (135), a first side adjustable strap tab (140), a middle adjustable strap (145), a middle adjustable strap tab (150), a back second side shoulder harness strap (155), a back first side shoulder harness strap (160), a back upper connecting panel (165), a back middle connecting panel, a back lower connecting panel (175), a second restraint buckle (180), a first restraint buckle (185), a middle restraint buckle (190), a back accessory pouch (195), a back accessory pouch front panel (200), a back accessory pouch flap (205), an ankle restraint cuff (210), an ankle restraint cuff loop (215), a first accessory hand restraint (220), an arm accessory restraint (225), a first arm adjustable length cuff (230), a second arm adjustable length cuff (235), an adjustable length connecting strap (240), a second restraint buckle securing point (245), a first restraint buckle securing point (250), a middle restraint buckle securing loop (255), a middle restraint buckle securing point (260), a restraint buckle release tool (265), a second hand-restraint retaining ring (270), an ankle restraint cuff distinguishable lift tab (275), a restraint buckle recessed release mechanism (280), a front midpoint securing loop (285), a back midpoint securing loop (290), and a second accessory hand restraint (295).

Figure 3:
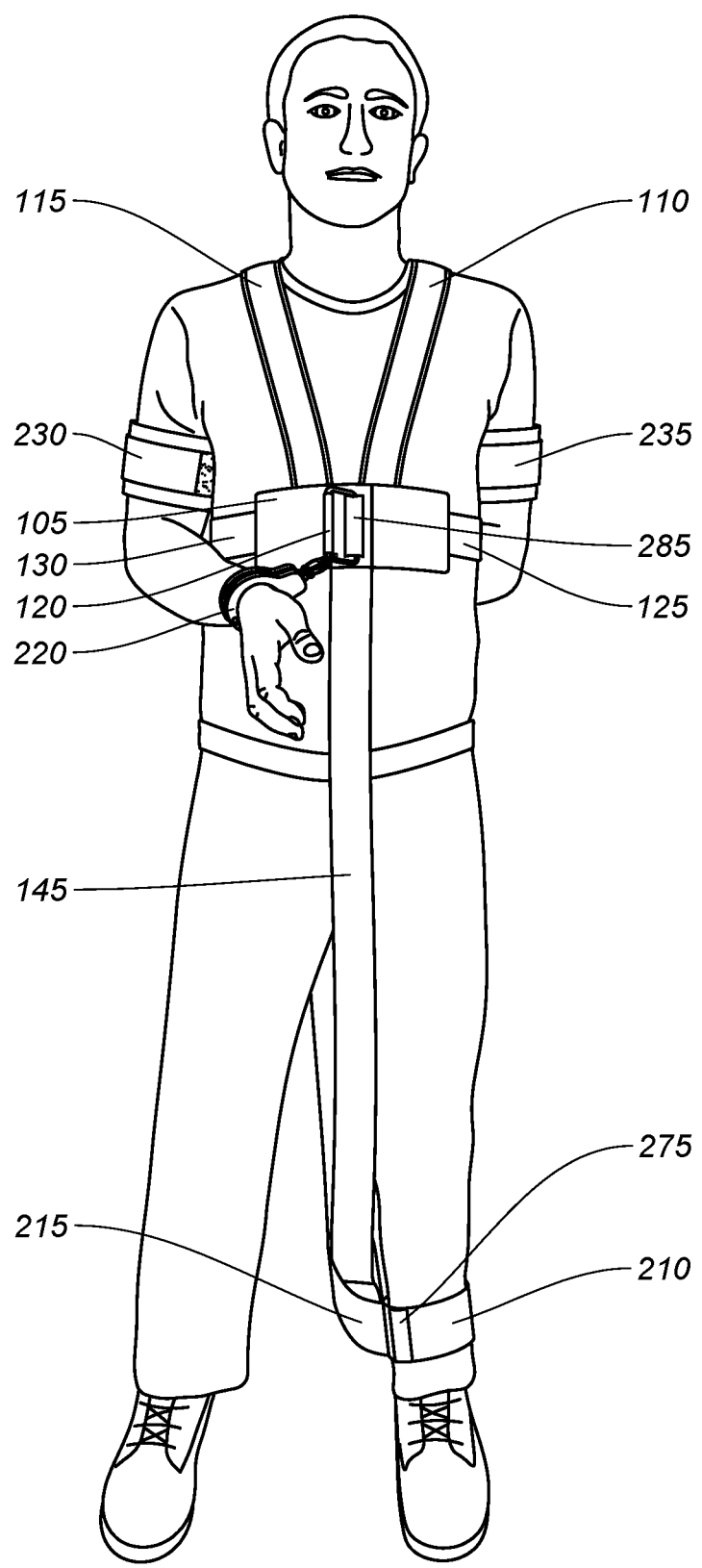
FIG. 3 shows a front view of a safe mobility transport harness secured around a person's torso with an ankle cuff around one leg of the person and an ankle restraint strap from the strap safe mobility transport harness secured to the ankle cuff.

FIG. 3 shows a front view of a safe mobility transport harness secured around a person's torso with an ankle restraint cuff around one leg of the person and an ankle restraint strap from the strap safe mobility transport harness secured to the ankle cuff.

Shown in FIG. 3 are the safe mobility transport harness (100), a front connecting panel (105), a front second side shoulder harness strap (110), a front first side shoulder harness strap (115), first hand-restraint retaining ring (120), a second side adjustable strap (125), a first side adjustable strap (130), a middle adjustable strap (145), an ankle restraint cuff (210), an ankle restraint cuff loop (215), a first accessory hand restraint (220), and portions of an arm accessory restraint (225) comprising a first arm adjustable length cuff (230) and a second arm adjustable length cuff (235). The arm restraint (225) can be configured to be hidden within clothing for a restrained person to appear (be visibly) non-restrained.

Figure 4:
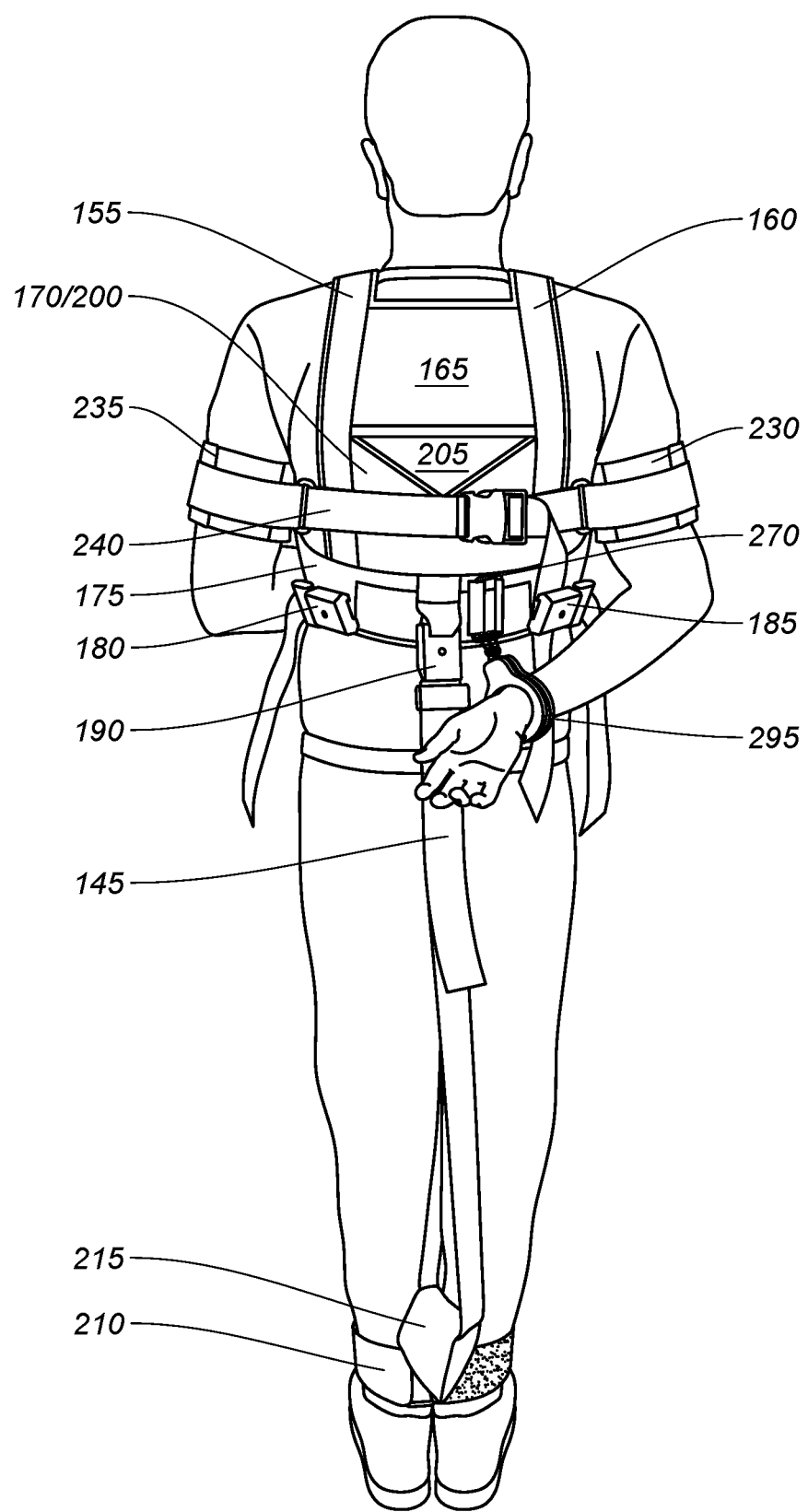
FIG. 4 shows a back view of a safe mobility transport harness secured around a person's torso with an ankle cuff around both legs of the person and an ankle restraint strap from the strap safe mobility transport harness secured to the ankle cuff.

FIG. 4 shows a back view of a safe mobility transport harness secured around a person's torso with an ankle cuff around both legs of the person and an ankle restraint strap from the strap safe mobility transport harness secured to the ankle cuff.

Shown in FIG. 4 are the safe mobility transport harness (100), a middle adjustable strap (145), a back second side shoulder harness strap (155), a back first side shoulder harness strap (160), a back upper connecting panel (165), a back middle connecting panel (170), a back lower connecting panel (175), a second restraint buckle (180), a first restraint buckle (185), a middle restraint buckle (190), a back accessory pouch (195), a back accessory pouch front panel (200), a back accessory pouch flap (205), an ankle restraint cuff (210), an ankle restraint cuff loop (215), a first arm adjustable length cuff (230), a second arm adjustable length cuff (235), a adjustable length connecting strap (240), a second hand-restraint retaining ring (270), and a second accessory hand restraint (295).

Figure 5:
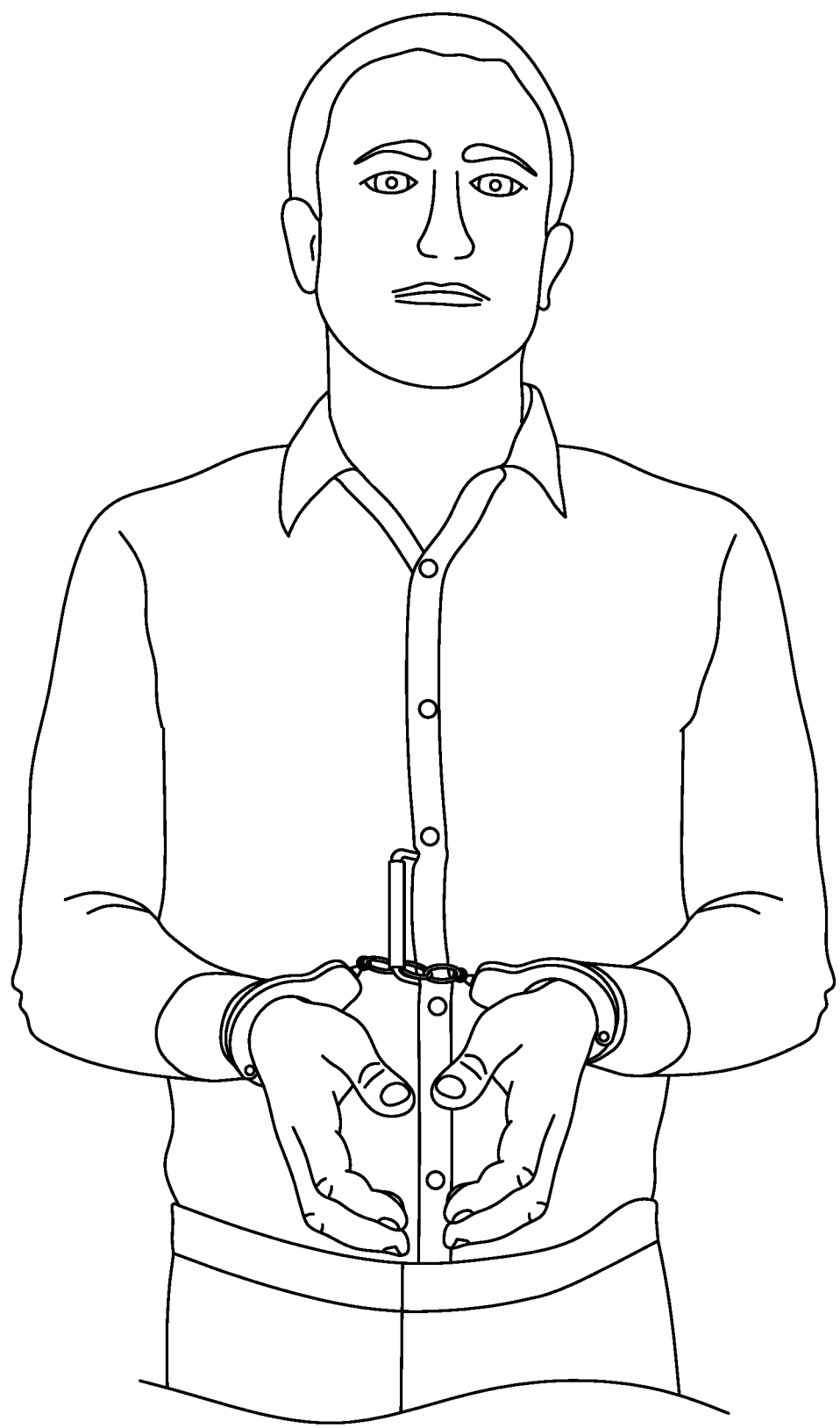
FIG. 5 shows a front view of a safe mobility transport harness secured in stealth mode under a person's clothing (configured to be hidden within clothing) and yet securing the person's hand, thereby enabling a person to appear (configured to be visibly non-restrained) or mostly unrestrained (minimally restrained) and yet safely restrained.

FIG. 5 shows a front view of a safe mobility transport harness secured in stealth mode under a person's clothing (configured to be hidden within clothing) and yet securing the person's hand, thereby enabling a person to appear (configured to be visibly non-restrained) or mostly unrestrained (minimally restrained) and yet safely restrained.

The safe mobility transport harness (100) functions for safely restraining persons to avoid injury to others and to the restrained person while allowing mobility and transport.

The front connecting panel (105) functions for connecting together and safely limiting movement of harness and panel straps of the safe mobility transport harness.

The front second side shoulder harness strap (110) functions for connecting together and safely limiting movement of the front connecting panel to a back connecting panel via a person's second shoulder.

The front first side shoulder harness strap (115) functions for connecting together and safely limiting movement of the front connecting panel to a back connecting panel via a person's first shoulder.

The front second side shoulder harness strap (110) is angularly affixed to a top side of the front connecting panel (105) and to the back second side shoulder harness strap (155), which is angularly affixed to a top second side edge of the back lower connecting panel (175).

The front first side shoulder harness strap (115) is angularly affixed to a top side of the front connecting panel (105) and to the back first side shoulder harness strap (160), which is angularly affixed to a top first side edge of the back lower connecting panel (175).

The second side adjustable strap (125) is affixed at a proximal end to a second side of the front connecting panel (105) and comprises a second side adjustable strap tab (135) for connecting to a second restraint buckle (180), which is affixed to a second restraint buckle securing point (245) which is affixed to a second side of the back lower connecting panel (175), for securely connecting to and for safely limiting movement of the front connecting panel (105) with respect to the back lower connecting panel (175).

The first side adjustable strap (130) is affixed at a proximal end to a first side of the front connecting panel (105) and comprises a first side adjustable strap tab (140) for connecting to a first restraint buckle (185), which is affixed to a first restraint buckle securing point (250) which is affixed to a first side of the back lower connecting panel (175), for securely connecting to and for safely limiting movement of the front connecting panel (105) with respect to the back lower connecting panel (175).

The first hand-restraint retaining ring (120) is attached at a front midpoint securing loop (285) of the front connecting panel (105) for securely limiting motion of a first accessory hand restraint (220) and functions for connecting together and safely limiting movement of an accessory hand restraint to the front connecting panel.

The second side adjustable strap (125) functions for connecting together and safely limiting movement of the front connecting panel to a back connecting panel via a person's second side.

The first side adjustable strap (130) functions for connecting together and safely limiting movement of the front connecting panel to a back connecting panel via a person's first side.

The second side adjustable strap tab (135) functions for connecting together and safely limiting movement of the second side adjustable strap to a second restraint buckle affixed to a back connecting panel.

The first side adjustable strap tab (140) functions for connecting together and safely limiting movement of the first side adjustable strap to a first restraint buckle affixed to a back connecting panel.

The middle adjustable strap (145) functions for connecting together and safely limiting movement of the front connecting panel to a back connecting panel and limiting leg mobility.

The middle adjustable strap tab (150) functions for connecting together and safely limiting movement of the middle adjustable strap to a middle security buckle affixed to a back connecting panel and limiting leg mobility.

The middle adjustable strap (145) has a length of at least 60 inches and is affixed at a proximal end to a lower side of the front connecting panel (105) and comprises a middle adjustable strap tab (150) for connecting to a middle restraint buckle (190) which is affixed to a middle restraint buckle securing loop (255), which is affixed to middle restraint buckle securing point (260) which is affixed to a top side of the back lower connecting panel (175) to affix the middle restraint buckle (190) to the back lower connecting panel (175), wherein the middle adjustable strap (145) is configured for passing (can be passed) through an ankle restraint cuff loop (215) of an ankle restraint cuff (210) which is configured for encircling at least one leg of a restrained person to prevent unauthorized leg movement of the restrained person, such as running, attempting to escape or using his or her legs to suddenly or unexpected kick another person and yet to safely and easily adjust the middle adjustable strap (145) to allow for authorized, safe and limited movement of the restrained person, such as walking.

The back second side shoulder harness strap (155) functions for connecting together and safely limiting movement of a back connecting upper to the front connecting panel via a person's second shoulder.

The back first side shoulder harness strap (160) functions for connecting together and safely limiting movement of a back connecting panel to the front connecting panel via a person's first shoulder.

The back upper connecting panel (165) functions for connecting together and safely limiting movement of the first and second shoulder harness straps to a back connecting panel-middle.

The back middle connecting panel (170) is affixed at a lower side to the top side of the back lower connecting panel (175) and affixed at a top side to a bottom edge of a back upper connecting panel (165), both comprising second edges affixed to the back second side shoulder harness strap (155) and comprising first edges affixed to the back first side shoulder harness strap (160) with the back middle connecting panel (170) further comprising a back accessory pouch (195) for keeping restraining accessories within the back accessory pouch (195) and comprising a back accessory pouch front panel (200) and a back accessory pouch flap (205) and functions for connecting together and safely limiting movement of the back upper connecting panel to a back lower connecting panel and providing support for the back accessory pouch.

The back lower connecting panel (175) functions for connecting together and safely limiting movement of the first, second and middle adjustable straps of the safe mobility transport harness.

The second restraint buckle (180) functions for connecting together and safely limiting movement of the second side adjustable strap to the back connecting panels and preventing release except with a buckle restraint release tool.

The first restraint buckle (185) functions for connecting together and safely limiting movement of the first side adjustable strap to the back connecting panels and preventing release except with a buckle restraint release tool.

The middle restraint buckle (190) functions for connecting together and safely limiting movement of the middle adjustable strap to the back connecting panels and preventing release except with a buckle restraint release tool.

The back accessory pouch (195) functions for provides safe accessory storage to law enforcement officers while preventing access to restrained persons.

The back accessory pouch front panel (200) functions for keeping accessories within accessory pouch.

The back accessory pouch flap (205) functions for keeping accessories within accessory pouch.

The ankle restraint cuff (210) functions for restraining a person's legs to prevent unauthorized leg movement and injurious and damaging activity by a restrained person while permitting limited leg mobility, such as walking.

The ankle restraint cuff loop (215) functions for securing the ankle restraint cuff to prevent unauthorized leg movement and injurious and damaging activity by a restrained person using the middle adjustable strap which is affixed to the front connecting panel and connected to the back connecting panel.

The first accessory hand restraint (220) functions for restraining a person's hands to prevent injurious and damaging activity by a restrained person while allowing limited motion. The first accessory hand restraint may be used to less the appearance of restraint.

The arm accessory restraint (225) comprises a first arm adjustable length cuff (230) and a second arm adjustable length cuff (235) and an adjustable length connecting strap (240) and function for safely limiting movement of a person's arms while allowing authorized, safe, limited motion. The arm restraint (225) can be enclosed (configured to be hidden) within clothing so a restrained person can be configured to appear (is visibly) non-restrained.

The first arm adjustable length cuff (230) functions for restraining a person's first arm to prevent injurious and damaging activity by a restrained person while allowing authorized, safe, limited motion. The first arm adjustable length cuff (230) can be enclosed (configured to be hidden)

within clothing so a restrained person can be configured to appear (is visibly) non-restrained.

The second arm adjustable length cuff (235) functions for restraining a person's second arm to prevent injurious and damaging activity by a restrained person while allowing authorized, safe, limited motion. The second arm adjustable length cuff (235) can be enclosed (configured to be hidden) within clothing so a restrained person can be configured to appear (is visibly) non-restrained.

The adjustable length connecting strap (240) functions for connecting together a person's arms while safely limiting movement of a person's arms while allowing authorized, safe, limited motion. The adjustable length connecting strap (240) can be enclosed (configured to be hidden) within clothing so a restrained person can be configured to appear (is visibly) non-restrained.

The second restraint buckle securing point (245) functions for securing second restraint buckle (180) to the back lower connecting panel (175).

The first restraint buckle securing point (250) functions for securing first restraint buckle (185) to the back lower connecting panel (175).

The middle restraint buckle securing loop (255) functions for securing middle restraint buckle (190) to the back lower connecting panel (175).

The middle restraint buckle securing point (260) functions for securing middle restraint buckle (190) to the back lower connecting panel (175).

The restraint buckle release tool (265) comprises a tip of length at least 0.1 inches and a width between 0.1 inch and 0.25 inch inclusive and withstands a force of at least 2 ounces without deflection to disengage the restraint buckle recessed release mechanism (280) and functions for releasing the second side adjustable strap tab (135) from the second restraint buckle (180), (180), the first side adjustable strap tab (135) from the first restraint buckle (180), (185) and the middle adjustable strap tab (150) from middle restraint buckle (190). The restraint buckle release tool (265) may have one or more tips. A tip may a configuration of one or more points or edges, including a single point tip, a rounded tip, a round tip, a triangular tip, a square tip, a hexagonal tip, etc.

The second hand-restraint retaining ring (270) is attached at a back midpoint securing loop (290) of the back lower connecting panel (175) for securely limiting motion of a second accessory hand restraint (295) and functions for connecting together and safely limiting movement of a hand restraint to the back lower connecting panel.

The ankle restraint cuff distinguishable lift tab (275) functions for easily disengaging the ankle restraint cuff (210).

The second restraint buckle (180), the first restraint buckle (185) and the middle restraint buckle (190) each comprise a restraint buckle recessed release mechanism (280) which requires a restraint buckle release tool (265), both of which are sized from 0.1 inch to 0.25 inch to separately release each of the second restraint buckle (180), the first restraint buckle (185) and middle restraint buckle (190) while preventing undesired, i.e., accidental or unauthorized, release of the second side adjustable strap tab (135) from the second restraint buckle (180), the first side adjustable strap tab (140) from the first restraint buckle (185), and the middle adjustable strap (145) from the middle restraint buckle (190). The restraint buckle recessed release mechanism (280) functions effectively for preventing release of buckle except with a buckle release tool.

The front midpoint securing loop (285) functions for securing a first hand-restraint retaining ring to a front connecting panel.

The back midpoint securing loop (290) functions for securing a second hand-restraint retaining ring to a back lower connecting panel.

The second accessory hand restraint (295) functions for restraining a person's hands to prevent injurious and damaging activity by a restrained person while allowing limited motion. The first accessory hand restraint may be used to less the appearance of restraint.

The safe mobility transport harness (100) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The front connecting panel (105) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The front second side shoulder harness strap (110) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The front first side shoulder harness strap (115) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The first hand-restraint retaining ring (120) may be made of any material providing sufficient strength to connect together and safely limit movement of a hand restraint to the front connecting panel. The material may be made of steel, iron or a hard and durable plastic.

The second side adjustable strap (125) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The first side adjustable strap (130) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The second side adjustable strap tab (135) may be made of any material providing sufficient strength to connect together and safely limit movement of the second side adjustable strap to a second restraint buckle affixed to a back connecting panel. The material may be a metal, such as steel or iron. The material may be a hard and durable plastic.

The first side adjustable strap tab (140) may be made of any material providing sufficient strength to connect together and safely limit movement of the first side adjustable strap to a first restraint buckle affixed to a back connecting panel. The material may be a metal, such as steel or iron. The material may be a hard and durable plastic.

The middle adjustable strap (145) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The middle adjustable strap tab (150) may be made of any material providing sufficient strength to connect together and safely limit movement of the middle adjustable strap to a middle restraint buckle affixed to a back connecting panel. The material may be a metal, such as steel or iron. The material may be a hard and durable plastic.

The back second side shoulder harness strap (155) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The back first side shoulder harness strap (160) may be made from any material providing sufficient strength to connect together and safely limiting movement of the front connecting panel with respect to the back connecting panel. The material may be ballistic nylon, a re-enforced fiber, such as re-enforced cotton, or other flexible material with sufficient strength to prevent rips or tearing during use.

The back upper connecting panel (165) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The back middle connecting panel (170) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The back lower connecting panel (175) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The second restraint buckle (180) may be made from a hard and durable material, such as metal, including but not limited to most grades of steel, iron, or other hard and durable material. The restraint buckle may have an internal spring as part of a release mechanism, which should also be hard, durable, strong, and resilient to absorb contraction forces without breaking, and maintain locking of the restraint buckle to the adjustable strap tab.

The first restraint buckle (185) may be made from a hard and durable material, such as metal, including but not limited to most grades of steel, iron, or other hard and durable material. The restraint buckle may have an internal spring as part of a release mechanism, which should also be hard, durable, strong, and resilient to absorb contraction forces without breaking, and maintain locking of the restraint buckle to the adjustable strap tab.

The middle restraint buckle (190) may be made from a hard and durable material, such as metal, including but not limited to most grades of steel, iron, or other hard and durable material. The restraint buckle may have an internal spring as part of a release mechanism, which should also be hard, durable, strong, and resilient to absorb contraction forces without breaking, and maintain locking of the restraint buckle to the adjustable strap tab.

The back accessory pouch (195) may be made from any material providing sufficient strength to retain small devices, such as handcuffs, wrist ties, restraint buckle release tool, spare parts, etc. within the pouch without ripping, tearing, or suffering a puncture.

The back accessory pouch front panel (200) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The back accessory pouch flap (205) may be made from any material providing sufficient strength to retain small devices, such as handcuffs, wrist ties, restraint buckle release tool, spare parts, etc. within the pouch without ripping, tearing, or suffering a puncture.

The ankle restraint cuff (210) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The ankle restraint cuff loop (215) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The first accessory hand restraint (220) may be made from any material providing sufficient strength to safely restraining persons to avoid injury to others and to the restrained person while allowing mobility and transport. The material may be metal, ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The arm accessory restraint (225) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The first arm adjustable length cuff (230) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The second arm adjustable length cuff (235) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The adjustable length connecting strap (240) may be made from any material providing sufficient strength to safely restraining persons to avoid injury to others and to the restrained person while allowing mobility and transport. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The second restraint buckle securing point (245) may be made from any material providing sufficient strength to secure the second restraint buckle (180) to the back lower connecting panel (175). The material may be ballistic nylon, a re-enforced fiber, such as re-enforced cotton, or other flexible material with sufficient strength to prevent rips or tearing during use.

The first restraint buckle securing point (250) may be made from any material providing sufficient strength to secure the first restraint buckle (185) to the back lower connecting panel (175). The material may be ballistic nylon, a re-enforced fiber, such as re-enforced cotton, or other flexible material with sufficient strength to prevent rips or tearing during use.

The middle restraint buckle securing loop (255) may be made from any material providing sufficient strength to secure the middle restraint buckle (190) to the back lower connecting panel (175). The material may be ballistic nylon, a re-enforced fiber, such as re-enforced cotton, or other flexible material with sufficient strength to prevent rips or tearing during use.

The middle restraint buckle securing point (260) may be made from any material providing sufficient strength to secure the middle restraint buckle (190) to the back lower connecting panel (175). The material may be ballistic nylon, a re-enforced fiber, such as re-enforced cotton, or other flexible material with sufficient strength to prevent rips or tearing during use.

The restraint buckle release tool (265) may be made of any material providing sufficient strength without breaking to engage a release mechanism of the restraint buckles to facilitate release of the adjustable strap tabs from the restraint buckles. The restraint buckle release tool may be made of a metal, such as steel or iron, or of a hard and durable plastic. The restraint buckle release tool may have a blunt end, a flat end, or an uneven end. The restraint buckle release tool has a tip width of 0.10 inch to 0.25 inch to engage the restraint buckle release mechanism.

The second hand-restraint retaining ring (270) may be made of any material providing sufficient strength to connect together and safely limit movement of a hand restraint to the back connecting panel. The material may be made of steel, iron or a hard and durable plastic.

The ankle restraint cuff distinguishable lift tab (275) may be made of any material capable of distinguishing a proximal end section of the ankle restraint cuff (210) from an inner section of the ankle restraint cuff (210) for easy removal. The distinguishable lift tab may have one or more of a different color, different texture, or different markings from the ankle accessory restraint cuff.

The restraint buckle recessed release mechanism (280) may be made of any material providing sufficient strength without breaking to engage, hold, and to release a adjustable side strap tab (135, 140, 150) of the adjustable side straps (125, 130, 145) to the restraint buckles (180, 185, 190). The restraint buckle recessed release mechanism (280) may be made of a metal, such as steel or iron, or of a hard and durable plastic. The restraint buckle recessed release mechanism (280) have an internal spring which should also be hard, durable, strong, and resilient to absorb contraction forces without breaking, and maintain locking of the adjustable strap tabs (135, 140, 150) and may be made of a metal, such as steel or iron, or of a hard and durable plastic.

The front midpoint securing loop (285) may be made of any material providing sufficient strength to secure a hand restraint to the connecting panel. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The back midpoint securing loop (290) may be made of any material providing sufficient strength to secure a hand restraint to the connecting panel. The material may be ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

The second accessory hand restraint (295) may be made from any material providing sufficient strength to safely restraining persons to avoid injury to others and to the restrained person while allowing mobility and transport. The material may be metal, ballistic nylon, a re-enforced fiber, such as re-enforced cotton, or other flexible material with sufficient strength to prevent rips or tearing during use. The re-enforcement may be with coated wires of metal or other flexible material, insert panels between layers of outer material, or other material with sufficient strength to prevent rips or tearing during use.

These descriptions and drawings are embodiments and teachings of the disclosure. All variations are within the spirit and scope of the disclosure. This disclosure is not to be considered as limiting the claims to only the embodiments illustrated or discussed. Certain changes can be made in the subject matter without departing from the spirit and the scope of this invention. It is realized that changes are possible within the scope of this invention and it is further intended that each structure or element recited in any of the claims is to be understood as referring to all equivalent structure or elements. The following claims are intended to cover the invention as broadly as possible in whatever form it may be used.

We claim:

1. A safe mobility transport harness (100) for safely restraining a person without injury to the restrained person and other persons comprising:
   (a) a front connecting panel (105) connected to and for safely limiting movement of a plurality of straps comprising a front second side shoulder harness strap (110), a front first side shoulder harness strap (115), a back second side shoulder harness strap (155), a back first side shoulder harness strap (160), a second side adjustable strap (125), a first side adjustable strap (130) and a middle adjustable strap (145) for affixing to a back lower connecting panel (175) of the safe mobility transport harness (100),
   (b) wherein the front second side shoulder harness strap (110) is angularly affixed to a top side of the front connecting panel (105) and to the back second side shoulder harness strap (155), which is angularly affixed to a top second side edge of the back lower connecting panel (175),
   (c) wherein the front first side shoulder harness strap (115) is angularly affixed to a top side of the front connecting panel (105) and to the back first side shoulder harness strap (160), which is angularly affixed to a top first side edge of the back lower connecting panel (175),
   (d) wherein the second side adjustable strap (125) is affixed at a proximal end to a second side of the front connecting panel (105) and comprises a second side slideably adjustable strap tab (135) for connecting to a second restraint buckle (180), which is affixed to a second restraint buckle securing point (245) which is affixed to a second side of the back lower connecting panel (175), for securely connecting to and for safely limiting movement of the front connecting panel (105) with respect to the back lower connecting panel (175) and the second side adjustable strap (125) is slideably adjustable to allow for adjustable and safe restraint with limited movement of a restrained person exclusive of encompassing a person's arms,
   (e) wherein the first side adjustable strap (130) is affixed at a proximal end to a first side of the front connecting panel (105) and comprises a first side slideably adjustable strap tab (140) for connecting to a first restraint buckle (185), which is affixed to a first restraint buckle securing point (250) which is affixed to a first side of the back lower connecting panel (175), for securely connecting to and for safely limiting movement of the front connecting panel (105) with respect to the back lower connecting panel (175) and the first side adjustable strap (130) is slideably adjustable to allow for adjustable and safe restraint with limited movement of the restrained person exclusive of encompassing a person's arms,
   (f) wherein the middle adjustable strap (145) has a length of at least 60 inches and is affixed at a proximal end to a lower side of the front connecting panel (105) and comprises a middle slideably adjustable strap tab (150) for connecting to a middle restraint buckle (190) which is affixed to a middle restraint buckle securing loop (255), which is affixed to a middle restraint buckle securing point (260) which is affixed to a top side of the back lower connecting panel (175) to affix the middle restraint buckle (190) to the back lower connecting panel (175), wherein the middle adjustable strap (145) can be passed through an ankle restraint cuff loop (215) of an ankle restraint cuff (210) for encircling at least one leg of a restrained person to prevent the restrained person from unauthorized use of his or her legs without producing undesirable pressure on restrained person's crotch and the middle adjustable strap (145) is non-automatically slideably adjustable for retracting and lengthening the middle adjustable strap (145) to allow for safe and limited leg movement of the restrained person for walking without encompassing a restrained person's upper legs, and the middle adjustable strap (145) may be adjusted at the back lower connecting panel (175) to adjust mobility of a restrained person while ensuring safety of an adjusting person from being kicked or kneed by the restrained person,
   (g) a first hand-restraint retaining ring (120) sized for accommodating handcuffs through the first hand-restraint retaining ring (120) and attached along its entire length at a front midpoint securing loop (285) of the front connecting panel (105) for securely limiting motion of a first accessory hand restraint (220),
   (h) a second hand-restraint retaining ring (270) sized for accommodating handcuffs through the second hand-restraint retaining ring (270) and attached along its entire length at a back midpoint securing loop (290) of the back lower connecting panel (175) for securely limiting motion of a second accessory hand restraint (295),
   (i) a back middle connecting panel (170) affixed at a lower side to the top side of the back lower connecting panel (175) and affixed at a top side of the back middle connecting panel (170) to a bottom edge of a back upper connecting panel (165), the back middle connecting panel (170) and the back upper connecting panel (165) comprising second edges affixed to the back second side shoulder harness strap (155) and comprising first edges affixed to the back first side shoulder harness strap (160) with the back middle connecting panel (170) further comprising a back accessory pouch (195) sized for keeping restraining accessories within the back accessory pouch (195) and comprising a back accessory pouch front panel (200) and a back accessory pouch flap (205), (j) wherein the second restraint buckle (180), the first restraint buckle (185) and the middle restraint buckle (190) each comprise a restraint buckle recessed release mechanism (280) which requires a restraint buckle release tool (265) to separately release each of the second restraint buckle (180), the first restraint buckle (185) and the middle restraint buckle (190) to prevent undesired release of the second side adjustable strap tab (135) from the second restraint buckle (180), the first side adjustable strap tab (140) from the first restraint buckle (185), and the middle adjustable strap tab (150) from the middle restraint buckle (190)

(k) wherein the front connecting panel (105) and the back lower connecting panel (175) comprise right angle parallelograms and are together with the second side adjustable strap (125) and the first side adjustable strap (130) are collectively positionable across and around a person's abdomen, back, and sides respectively as to not cause chest compression and to allow air circulation around a restrained person's torso as to not cause heat exhaustion, and (l) the front second side shoulder harness strap (110) and the front first side shoulder harness strap (115) are spaced apart at the front connecting panel (105) by a width of the middle adjustable strap (145), and diverge from the front connecting panel (105) on either side of a restrained person's neck to the back second side shoulder harness strap (155) and the back first side shoulder harness strap (160) respectively, which diverge to the back lower connecting panel (175) and are spaced apart by the back middle connecting panel (170) as to prevent carotid compression and choking of a restrained person, irrespective of a restrained person's upright, prone, supine or lateral position.

2. The safe mobility transport harness (100) of claim 1 wherein the ankle restraint cuff (210) is configured for encircling at least one leg of a restrained person and comprises an ankle restraint cuff loop (215) wherein the middle adjustable strap (145) is configured for passing through the ankle restraint cuff loop (215) and when secured with the middle adjustable strap tab (150) to the middle restraint buckle (190) restrains leg mobility of the restrained person to prevent unauthorized leg movement while permitting the restrained person authorized and limited leg mobility for walking and further comprising an ankle restraint cuff distinguishable lift tab (275) to readily distinguish a proximal end of the ankle restraint cuff (210) from an inner portion of the ankle restraint cuff (210) for when the ankle restraint cuff (210) is encircling at least one leg of a restrained person with the ankle restraint cuff distinguishable lift tab (275) secured to the ankle restraint cuff (210).

3. The safe mobility transport harness (100) of claim 1 further comprising an arm restraint (225) unconnectable to the front connecting panel (105), the back connecting panel (175), the second side adjustable strap (125) and the first side adjustable strap (130) for concurrent restraint of a person's elbows exclusive of the hands comprising a first arm adjustable length cuff (230) and a second arm adjustable length cuff (235) and an adjustable length connecting strap (240) for safely limiting movement of a person's arms to prevent a restrained person from use of an elbow to inflict injury while allowing limited motion.

4. The safe mobility transport harness (100) of claim 1 wherein the restraint buckle release tool (265) comprises a non-handcuff key tip of length at least 0.1 inches and a width between 0.1 inch and 0.25 inch inclusive and withstands a force of at least 2 ounces without deflection to disengage the restraint buckle recessed release mechanism (280).

5. The safe mobility transport harness (100) of claim 1 wherein safe mobility transport harness (100) is configured to be hidden within clothing for a restrained person to be visibly minimally restrained.

6. The safe mobility transport harness (100) of claim 3 wherein the arm restraint (225) is configured to be hidden within clothing for a restrained person to be visibly minimally non-restrained.

7. The safe mobility transport harness (100) of claim 1 wherein the restraint buckle recessed release mechanism (280) is sized from 0.1 inch to 0.25 inch to separately release each of the second restraint buckle (180), the first restraint buckle (185) and middle restraint buckle (190) while preventing undesired release of the second side adjustable strap tab (135) from the second restraint buckle (180), the first side adjustable strap tab (140) from the first restraint buckle (185), and the middle adjustable strap (145) from the middle restraint buckle (190).

* * * * *